United States Patent [19]

Pearlstein et al.

[11] Patent Number: 5,502,270

[45] Date of Patent: Mar. 26, 1996

[54] STARCH AND GRAIN WITH A NOVEL GENOTYPE

[75] Inventors: Richard W. Pearlstein; James F. Ulrich, both of Newark, Del.

[73] Assignee: E. I. Du Pont de Nemours and Company, Wilmington, Del.

[21] Appl. No.: 40,333

[22] Filed: Mar. 30, 1993

[51] Int. Cl.$^6$ ............................... A01H 5/00; A01H 5/10; A01H 1/00

[52] U.S. Cl. ................. 800/200; 800/250; 800/DIG. 56

[58] Field of Search ................................. 800/200, 250, 800/DIG. 56, 230, 235; 47/58.03

[56] References Cited

U.S. PATENT DOCUMENTS

| | | | |
|---|---|---|---|
| 4,789,557 | 12/1988 | Friedman et al. | 426/578 |
| 4,790,997 | 12/1988 | Friedman et al. | 426/578 |
| 5,004,864 | 4/1991 | Robertson et al. | 800/235 |
| 5,009,911 | 4/1991 | Mauro et al. | 426/578 |

OTHER PUBLICATIONS

Paulis et al. 1992. Theor. Appl. Genet. 85:407–414.

Garwood et al. 1972. Crop Science. 12:119–121.

Brockett, E. et al, "Gelatinization Characteristics of Starch from *du, wx, ae,* and *ae wx,* Endosperm of Sweet Corn Inbred 1a5125", Paper No. 7807, PA Agricultural Experimental Station Series, The Pennsylvania State University, University Park, PA. 1988.

Boyer, C. D. et al, "Interaction of the Amylose–Extender and Waxy Mutants of Maize", *The Journal of Heredity*, 67, 209–214, 1976.

Yamamada, T. et al, "A Novel type of Corn Starch from a Strain of Maize", *Starch/Stärke*, 30, 145–148, 1978.

*Primary Examiner*—David T. Fox
*Assistant Examiner*—Erich E. Veitenheimer

[57] ABSTRACT

Grain, produced by a starch bearing plant, which is heterozygous for the dull gene and homozygous recessive for the waxy and the amylose extender genes. The invention also relates to starch with novel functional properties obtained from such grain which can be utilized for foodstuffs and other applications without chemical modifications.

3 Claims, 4 Drawing Sheets

STARCH AND GRAIN WITH A NOVEL GENOTYPE

FIELD OF THE INVENTION

This invention relates to starch bearing plants and to starch which has been obtained from a grain or vegetative plant part heterozygous for the dull (du) gene and homozygous recessive for the amylose extender (ae) and waxy (wx) genes.

BACKGROUND OF THE INVENTION

Starch is a mixture of two polysaccharides, amylose and amylopectin. Amylose is an unbranched chain of up to several thousand α-D-glucopyranose units linked by α 1–4 glycosidic bonds. Amylopectin is a highly branched molecule made of up to 50,000 α-D-glucopyranose residues linked by α 1–4 and α 1–6 glycosidic bonds. Approximately 5% of the glycosidic linkages in amylopectin are α 1–6 bonds, which leads to the branched structure of the polymer.

Amylose and amylopectin molecules are organized into granules that are stored in plastids. The starch granules produced by most plants are 15–30% amylose and 75–85% amylopectin. The ratio of amylose to amylopectin and the degree of branching of amylopectin affects the physical and functional properties of the starch. Functional properties, such as viscosity and stability of a gelatinized starch, determine the usefulness and hence the value of starches in food and industrial applications. Where a specific functional property is needed, starches obtained from various crops such as maize, rice, or potatoes may meet the functionality requirements. If a starch does not meet a required functional property, for example it must have stable viscosity under high temperatures and acidic conditions, the functionality can sometimes be achieved by chemically modifying the starch. Various types and degrees of chemical modification are used in the starch industry, and the labelling and use of chemically modified starches must meet government regulations.

Within the starch bearing organs of plants, the proportion of amylose to amylopectin and the degree of branching of amylopectin are under genetic control. For example, plants homozygous recessive for the waxy gene lack a granule bound starch synthase enzyme and produce nearly 100% amylopectin. Plants homozygous recessive for the amylose extender gene can produce starch granules that are up to 90% amylose. The dull gene has been shown to control the production of a starch branching enzyme.

Genes that have their primary effect on starch or protein synthesis, including amylose extender (ae), brittle (bt), dull (du), floury (fl), horny (h), opaque (o), shrunken (sh), sugary (su), and waxy (wx), are referred to as recessive genes because their effect on kernel appearance can be masked in F1 seed by the presence of a dominant form of each respective gene. Conventional nomenclature of plant varieties has been established to identify genotypes that carry a particular gene of interest. For the previously listed genes, genotypes are identified by the homozygous recessive mutant alleles they carry. Other genes not listed in the variety name are homozygous dominant. For example, a variety described as ae wx is homozygous recessive for the amylose extender and waxy genes and homozygous dominant for the other starch biosynthesis genes such as brittle, dull, shrunken, and sugary. According to conventional genetics teaching, the effect of a recessive gene is not expressed unless the gene is homozygous recessive. Hence, reports on the properties of starch from mutant plant species typically describe starch obtained from plants homozygous recessive for a particular gene or combination of genes. The properties of starch obtained from maize plants homozygous recessive for ae, du, wx, and ae wx are reported in an article by E. Brockett et al. entitled "Gelatinization Characteristics of Starch from du, wx, ae, and ae wx Endosperm of Sweet Corn Inbred Ia5125", published in Starch/Starke 40 (1988) Nr. 5, pp. 175–177.

In cereal grains such as maize (*Zea mays* L.), the kernel is the product of double fertilization (Kiesselbach, T. A., 1980, The Structure and Reproduction of Corn, University of Nebraska Press). The pollen grain contains two sperm nuclei. At the time of fertilization one of the sperm nuclei fuses with the nucleus of the ovule to form the embryo of the seed, and one fuses with two female nuclei to form the endosperm of the seed. The endosperm receives two thirds of its genetic material from the female plant and one third from the pollen. The immediate effect of pollen on the developing seed is termed xenia. The number of copies of a particular gene present in a cell, such as an endosperm cell, is known as the gene dose. Gene dosage effects have been studied for the ae and wx genes. In non-waxy maize, the ae allele is usually completely recessive to the dominant allele Ae with respect to kernel appearance. In waxy maize, kernels with varying doses of the ae allele can often be visually distinguished from each other. The effect on starch properties of various doses of ae in waxy maize has been shown by T. Yamada et al. in an article entitled "A Novel Type of Corn Starch from a Strain of Maize" published in Starke 30 (1978) Nr. 5, pp. 145–148. The interaction of various doses of ae and wx on starch accumulation and apparent amylose content was reported by Boyer et al. in The Journal of Heredity, 67:209–214 1976. Two U.S. patents describe starch extracted from plants homozygous recessive for double or triple mutant gene combinations. For example, U.S. Pat. No. 4,789,557 relates to starch extracted from a plant homozygous recessive for the du and wx genes and U.S. Pat No. 5,009,911 relates to starch extracted from a plant homozygous recessive for the ae and wx genes. There have been no reports describing the use of starch obtained from heterozygous grain, nor reports of the effect of various doses of du on the pasting properties of starch.

Most cereal crops are handled as commodities, and many of the industrial and animal feed requirements for these crops can be met by common varieties which are widely grown and produced in volume. However, there exists at present a growing market for crops with special end-use properties which are not met by grain of standard composition. Most commonly, specialty maize is differentiated from "normal" maize, also known as field corn, by altered endosperm properties, such as an overall change in the degree of starch branching as in waxy or high amylose maize, an increased accumulation of sugars as in sweet corn, or an alteration in the degree of endosperm hardness as in food grade maize or popcorn; Glover, D. V. and E. T. Mertz, 1987, Corn. *In: Nutritional Quality of Cereal Grains; Genetic and Agronomic Improvement*, R. A. Olson and K. J. Frey, eds. American Society of Agronomy, Madison, Wis., pp. 183–336; Rooney, L. W. and S. O. Serna-Saldivar, 1987, *Food Uses of Whole Corn and Dry-Milled Fractions, In: Corn:Chemistry and Technology*, S. A. Watson and P. E. Ramstead, eds. American Association of Cereal Chemists, Inc., St. Paul, Minn., pp. 399–429. "Specialty" crops are typically grown under contract for specific end users who place value on starch quality or other specific quality attributes. A specialty crop such as waxy maize is more valuable as a raw material to the starch industry than is normal or commodity grade maize, and thus is referred to as a value added crop. Currently the market size and added value of waxy maize is such that approximately 150,000 acres are grown in the United States. Farmers are paid a premium for growing specialty crops such as waxy maize because it is more valuable than normal maize and must not be mixed with normal maize. The current invention offers the buyers of value added crops like waxy maize a source of starch having properties superior to waxy starch. Also, the invention offers farmers the opportunity to grow a higher value crop than normal or waxy maize.

Purified starch is obtained from plants by a milling process. Maize starch is extracted from kernels through the use of a wet milling process. Wet milling is a multi-step process involving steeping and grinding of the kernels and separation of the starch, protein, oil, and fiber fractions. A review of the maize wet milling process is given by S. R. Eckhoff in the *Proceedings of the Fourth Corn Utilization Conference*, Jun. 24–26, 1992, St. Louis, Mo., printed by the National Corn Growers Association, CIBA-GEIGY Seed Division and the United States Department of Agriculture. Purified starch is used in numerous food and industrial applications and is the major source of carbohydrates in the human diet. Typically, starch is mixed with water and cooked to form a thickened gel. Three important properties of a starch are the temperature at which it cooks, the viscosity the gel reaches, and the stability of the gel viscosity over time. The physical properties of unmodified starch during heating and cooling limit its usefulness in many applications. As a result, considerable effort and cost is needed to chemically modify starch in order to overcome a number of limitations of starch and to expand the usefulness of starch in industrial applications.

Some limitations of unmodified starches and properties of modified starches are given in Modified Starches: Properties and Uses, O. B. Wurzburg, ed., 1986, CRC Press, Inc., Boca Raton, Fla. Unmodified starches have very limited use in food products because the granules swell and rupture easily, thus forming weak bodied, undesirable gels. Depending on the food or industrial application, shortcomings of unmodified starches include excess or uncontrolled viscosity after cooking; cohesive or rubbery texture of cooked starch; structural break down during cooking or when exposed to shear or to low pH; and lack of clarity and the tendency of starch to become opaque and gel when cooled. Chemical modifications are used to stabilize starch granules thereby making the starch suitable for thousands of food and industrial applications including baby foods, powdered coffee creamer, surgical dusting powders, paper and yarn sizings, and adhesives, for example. Common chemical modifications include cross linking in which chemical bonds are introduced to act as stabilizing bridges between starch molecules, and substitution in which substituent groups such as hydroxyethyl, hydroxypropyl or acetyl groups are introduced into the starch molecules.

Cross linking and substitution are multi-step processes involving reactions that are usually run on aqueous suspensions of starch at wide ranges of temperature and pH. Cross linking reactions are often run for 1 to 5 hours at 40° C. to 50° C. and pH 8 to 12. However, cross linking under acidic conditions and for up to 28 hours is necessary for some applications; Wurzburg, O. B., 1986, *Cross-Linked Starches, In Modified Starches: Properties and Uses;* O. B Wurzburg, ed.; pp. 41–53. Cross linking reinforces hydrogen bonds in starch granules with chemical bonds between molecules. When aqueous suspensions of non-cross linked starches are heated, hydrogen bonds weaken, allowing water to enter the granules, causing them to swell, fragment, rupture, and collapse. When this happens, the starch develops a cohesive, rubbery texture. Cross linking reinforces the hydrogen bonds upon heating, thus providing varying degrees of granule stability, depending on the number of cross links. Cross linked starches are used to a wide extent in foods, paper, textiles, and adhesives. Other chemical modifications, such as substitutions, very often depend on cross linking to impart a desired property.

Cross-linked starches are used in foods, textiles, and adhesives, with the main use for high viscosity starches being as thickeners for food products; Jarowenko, W., 1986, *Acetylated Starch and Miscellaneous Organic Esters. In Modified Starches: Properties and Uses*, O. B. Wurzburg, ed., CRC Press, Boca Raton, Fla., pp. 55–77. Food starch thickeners must be stable under various conditions such as low pH, high speed mixing (shear), refrigeration, and freeze-thaw cycles. Cross linking provides resistance to low pH and shear, but the starches develop syneresis (lose water holding capacity) during refrigeration. Therefore, cross linking is often combined with substitution to improve the thickening performance of starch. Cross-linked starches are stabilized by the addition of substituents such as acetyl, phosphoryl, and hydroxypropyl groups. These cross-linked, substituted starches are used in baked, frozen, canned, and dry foods. Common uses are in pie fillings, gravies, custards, and cream fillings.

The use of chemically modified starches in the United States is regulated by the Food and Drug Administration (FDA). The Federal Food, Drug, and Cosmetic Act allows for two types of modified starches to be used in the food industry, "food starch-modified" and "industrial starch-modified". Food starch-modified may be used in food but must meet certain treatment limits, and industrial starch-modified may be used in items such as containers that come in contact with food and must also meet specified treatment requirements; Code of Federal Regulations, Title 21, Chapter 1, Part 172, *Food Additives Permitted in Food for Human Consumption,* Section 172, 892, Food Starch-Modified, U.S. Government Printing Office, Washington, D.C. 1981; (a) Part 178, *Indirect Food Additives,* Sect. 178.3520, Industrial Starch-Modified. These regulations limit the degree of chemical modification by defining the maximum amount of chemical reagent that can be used in the modification steps. The levels of by-products in starch resulting from the modification process are also regulated. For example, propylene chlorohydrin residues in hydroxypropyl starch are of special concern; Tuschhoff, J. V., 1986, *Hydroxypropylated Starches, In Modified Starches: Properties and Uses,* O. B. Wurzburg, ed., CRC Press, Boca Raton, Fla., pp. 55–77. At the present time, with the major expansion in new food products, there is a need for starches with greater stability and superior viscoelastic properties which can not be attained through chemical modification. Natural starch products, by eliminating chemical modification processes, would also save time, reduce costs, and minimize FDA regulatory approval time.

SUMMARY OF THE INVENTION

Applicants have discovered a starch with improved functional properties which does not require chemical modification. The starch is obtained from a grain involving a novel combination of the dull, waxy, and amylose extender genes produced by cross pollination of triple mutant ae du wx plants with double mutant ae wx plants, or vice versa.

Specifically, one aspect of the present invention is a grain produced by a starch bearing plant in which the genotype of the grain comprises a genome which is homozygous recessive for the waxy gene and the amylose extender gene, and heterozygous for the dull gene. Another aspect of the invention involves a method of making a thickened foodstuff by combining an effective amount of the starch extracted from the novel grain of Applicants' invention with water and a foodstuff and cooking the resulting composition as necessary to produce a thickened foodstuff. Maize is preferred as a starch bearing plant by virtue of established breeding strategies and widespread production.

BRIEF DESCRIPTION OF THE DRAWINGS

In FIG. 1, 'A' shows the elastic modulus at zero strain, 'B' the plasticity, 'C' the elastic modulus at 20% strain, 'D' the yield strain, 'E' the viscous modulus at zero strain, and 'F' the viscous modulus at 20% strain.

DESCRIPTION OF THE INVENTION

The present invention teaches that grain heterozygous at the du gene and homozygous recessive at the ae and wx genes will produce a starch with improved functional properties similar to chemically modified starch. Valuable properties of this new starch are a higher paste viscosity, greater shear resistance, and greater acid resistance than normal, waxy, du wx, ae wx, or ae du wx maize starch. The present invention teaches that the dull gene is not completely recessive in its effect on starch formation and on starch physical and functional properties.

A major advantage of the starch from a grain heterozygous for du and homozygous recessive for ae and wx is that it can be used as a thickener without being chemically modified. In industrial or food product applications where a specific functional property is needed, starches are most commonly altered by chemical modification. By reducing or eliminating the need for chemical modification, starch manufacturers will save money and food product manufacturers will be able to offer products containing natural food starch. This natural starch could be used in countries where some chemically modified food starches are prohibited by law.

Another valuable property of the starch of the present invention is that it has a creamy texture when cooked, making it suitable as a fat substitute. Recent medical research linking fat intake and obesity to health problems such as arteriosclerosis has prompted current dietary trends to reduce fat intake. The present invention will play a useful roll in food products that use starch-based fat substitutes. Fat has 2.25 times more energy measured as calories than starch, making starch-based fat substitutes very useful in low calorie food products.

Figure 1:
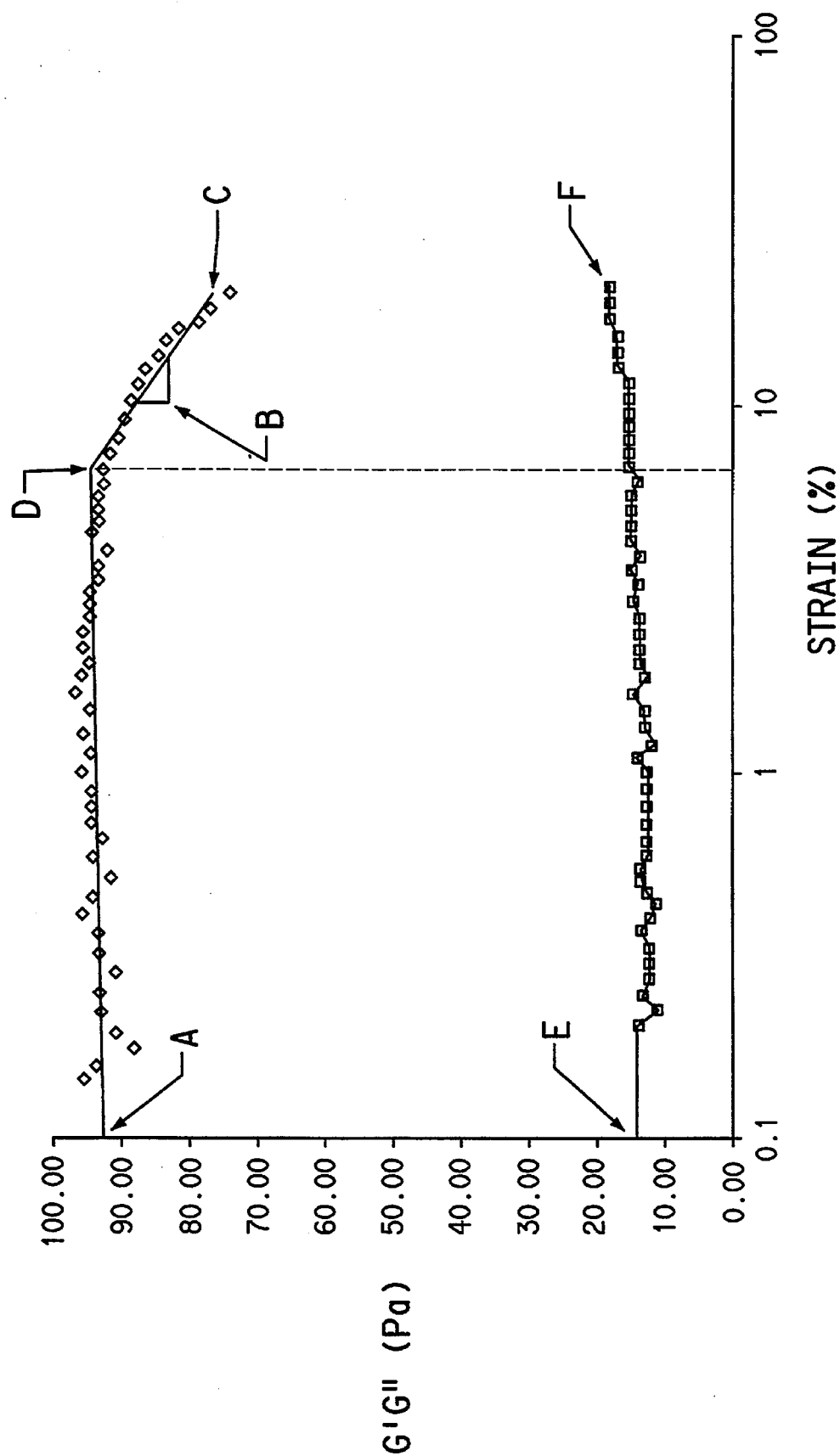
FIG. 1 shows the generalized behavior of a 5% (Dry Solids Basis) viscoelastic starch paste in which the elastic (G') and viscous (G") moduli, which are components of the viscosity of a gel, are plotted against the strain, which is a measure of the deformation of the gel.

In the context of this disclosure, a number of terms are used relevant to plant breeding and starch characterization. As used herein, the term "allele" refers to one of two or more forms of a gene that exists at a chromosome location, distinguished by their differing effects on the phenotype. "Chemically modified starch" refers to a starch that has been subjected to processes such as cross linking, derivitization, substitution, or other processes that involve chemical treatment to impart desired functional properties. A "female plant" is any plant incapable of producing or shedding viable pollen. The term "field corn" refers to the commonly grown commodity grade maize used for grain and/or forage, also known as dent corn when the kernels have an indented crown. "Gel quality" is a viscoelstic property of a gel measured by the ratio of viscous modulus to elastic modulus. If the ratio is 1 or greater, the material displays a more liquid-like than solid-like behavior (See FIG. 1). "Gel strength" is a viscoelastic property of a gel calculated from the elastic (G') and viscous (G") moduli using the following equation:

$$\text{Gel strength} = \sqrt{G'^2 + G''^2} \quad .$$

"Genome" refers to the entire set of genetic information found within a cell of an organism, while "genotype" is the genetic constitution in respect to the alleles at one, a few, or many of the alleles under observation.

Also relevant to this disclosure is the term "grain" which is the starch bearing, reproductive organ of a plant. In maize, grain is comprised of the mature kernels produced by growers for on farm use or for sale to customers while in potato and other tubers it is the vegetative plant part. The term "heterozygous" refers to a condition in which different alleles exist at corresponding loci on homologous chromosomes, while the term "homozygous" refers to a condition in which identical alleles exist at corresponding loci on homologous chromosomes. A "male plant" is a plant capable of shedding viable pollen. "Modulus" is the ratio of stress over strain, where stress is the applied force per unit area and strain is the change in length per unit length or change in volume per unit volume. Strain can also be referred to as shear. The elastic, or storage, modulus of a starch slurry is the component of rigidity contributed by the network of polymeric materials that make up the starch. The viscous, or loss, modulus is the component of rigidity of a starch slurry contributed by the fluid components (e.g., water molecules and non-entangled carbohydrate molecules) of the slurry. The characteristics and measurements of these parameters have been described previously; Hamann et al., *Applications of Thermal Scanning Rheology to the Study of Food Gels, In: Thermal Analysis of Foods;* V. R. Harwalkar and C. Y. Ma, ed.; pp. 306–332. As used herein, a "mutant" is a organism carrying a mutant gene, while a "mutant gene" is a gene that is in any way different from other, more frequently found forms of that gene. The term "pasting" refers to an irreversible physical change in starch granules or a suspension of starch granules characterized by swelling and hydration of granules, a rapid increase in viscosity of a suspension, and the formation of a sol from the suspension. This change is also known as cooking or gelatinization. The "phenotype" refers to the observable properties of an organism, produced by the interaction of the genotype and the environment. The term "plasticity" is a measure of the quality of a gel, measured as the rate of change of the elastic modulus in the nonlinear range of strain (See FIG. 1). As used herein, "polyploid" means a cell having more than two chromosome sets, or an organism composed of such cells. In maize, the kernel endosperm is triploid, a form of polyploidy in which each cell has three chromosome sets, two from the female parent and one from the male (pollen) parent. "Recessive" is a term describing an allele that is not phenotypically expressed in the heterozygous condition. "Reciprocal cross" refers to a paired cross in which two genotypes are crossed with each other, each genotype being used as both male and female. The term "semidominant" refers to a gene or mode of inheritance in which the phenotype of the heterozygous form lies between that of the the homozygous dominant and homozygous recessive form, i.e., it is intermediate. It is also known as partial dominance or incomplete dominance. The abbreviation "SNU" refers to the stirring number unit, approximately equal to 8 centipoise, which is a measure of viscosity. For conversion to SI units (pascal seconds), multiply centipoise by 1000, i.e., 1 PaSec=1000 cp. Hence, 1 SNU=0.008 PaSec. The term "sol" refers to a fluid colloidal system. The "viscosity" is a measure of the internal friction of a fluid that can be thought of as the consistency or thickness of a fluid. And finally, the "yield strain" refers to the strain at which a material starts displaying nonlinear viscoelastic behavior (See FIG. 1).

To produce heterozygous du and homozygous recessive ae wx grain, homozygous recessive ae du wx plants are cross pollinated with homozygous recessive ae wx plants or vice versa. The ae wx plants used to make the cross pollination are homozygous dominant for the du gene.

To develop a double mutant plant homozygous recessive for the ae and wx genes a plant carrying the recessive ae allele (Parent A) is crossbred with a plant carrying the recessive wx allele (Parent B). Progeny from this cross are grown and self pollinated, producing F2 generation seeds which carry both recessive genes. If Parent A and Parent B are homozygous recessive for ae and wx respectively, then 1/16 of the F2 progeny can be expected to be homozygous recessive for both genes. To develop a triple mutant plant homozygous for the ae wx and du genes, a double mutant ae wx plant (Parent C) is crossbred with a plant carrying the recessive du allele (Parent D). Progeny from this cross are grown and self pollinated. If Parent C is homozygous recessive for the ae and wx genes and Parent D is homozygous recessive for the du gene, then 1/64 of the F2 progeny can be expected to be homozygous recessive ae du wx.

In the present invention, the effect of one copy of the semi dominant Du allele from the pollen on the developing seed is two fold: to alter the physical and functional properties of the starch produced in the endosperm and to markedly increase starch accumulation compared to triple mutant ae du wx kernels. Triple mutant ae du wx kernels produce less than half the amount of starch of the heterozygous du grain. Because of the little amount of starch accumulation, the triple mutant aeduwx would not be grown commercially for starch production. To produce starch of the present invention, triple mutant ae du wx plants are cross pollinated with double mutant ae wx plants, or vice versa. If the double mutant is used as the male pollinator and the triple mutant is used as the female, the endosperm of the grain produced will have two copies of the recessive du allele and one copy of the semidominant Du allele. Also, starch extracted from this grain will cook at a lower temperature and will have a higher peak viscosity than starch of the reciprocal cross. The reciprocal cross is one in which an aewx plant is pollinated by an aeduwx plant, and the endosperm of this grain will have one copy of the recessive du allele and two copies of the semidominant Du allele. However, starch extracted from either cross will exhibit higher peak viscosity and lower cooking temperature than starch of homozygous aewx grain.

To facilitate cross pollination, the plants to be used as the female are rendered male sterile. This can be accomplished by physical removal of the male pollen-shedding part of the plant, by chemical treatment, or by a genetic mechanism such as cytoplasmic male sterility. In maize, the male part of the plant is the tassel which can be easily removed by hand or machine. Production of the present invention in maize requires planting male and female genotypes in adjacent rows in the field. Typically four rows of female plants alternate with one row of male plants. Female plants are rendered male sterile and are pollinated by male plants. Grain is harvested from female plants for subsequent starch extraction. This production method in which the direction of pollination is controlled results in seed that is genetically uniform. In contrast, in current grain production, random pollination occurs, resulting in non-uniform grain. Uniform grain quality is an important attribute to the grain milling industry.

Starch of the present invention could be produced in potato (*Solanum tuberosum* L.) and the heterozygous genotype could be maintained indefinitely by vegetative propagation. The double mutant ae wx and triple mutant ae du wx genotypes necessary to produce the present invention could be developed by several techniques. The mutant genes ae, du, and wx, could be introduced into potato plants in several ways including mutagenesis of seeds by treatment with ionizing radiation or chemical mutagens such as ethyl methane sulfonate, or by tissue culture induced somaclonal mutation. Most potato species are diploid (i.e., two chromosome sets), however, the most commonly grown species, *S. tuberosum*, is tetraploid (i.e., four chromosome sets). Genetic studies and the production of homozygous mutants are easier in diploid species than in tetraploid species. Diploid plants can be produced from tetraploid plants by several ways including interspecific or intergeneric hybridization, irradiation, chemical treatment, or anther and pollen culture; Schultz-Schaeffer, J., 1980, Cytogenetics—Plants, Animals, Humans, p. 245, Springer-Verlag New York Inc. Pollination of tetraploid *S. tuberosum* plants by diploid *S. phureja* plants often gives rise to seeds having diploid embryos derived from the female plant; Hoopes, R. W., and R. L. Plaisted, 1987, *Potato*, pp. 385–437, In: *Principles of Cultivar Development*, Vol. 2., W. R. Fehr, ed., Macmillan Publishing Company. In diploid plants, single mutants could be identified by starch analysis or by analyzing the enzymes controlled by ae, du, and wx. Once the single routants ae, du, or wx are identified in diploid plants, the conventional plant breeding strategies described previously could be used to combine the mutant genes into plants homozygous recessive for ae and wx and for ae, du, and wx. Diploid plants homozygous for ae and wx or ae, du, and wx can be cross pollinated to tetraploid plants. Diploid plants often produce unreduced gametes capable of fertilizing gametes of tetraploid plants thus resulting in tetraploid offspring. Progeny must be self pollinated to produce the necessary homozygous recessive double and triple mutant plants. Flowers of homozygous ae du wx tetraploid plants can be emasculated (anthers removed) and pollinated by homozygous ae wx tetraploid plants, or vice versa, to produce heterozygous plants in accordance with the present invention. The heterozygous plants can then be vegetatively propagated to produce tubers from which starch can be extracted.

EXAMPLES

The present invention is further defined in the following examples. It will be understood that the examples are given for illustration only and the present invention is not limited to uses described in the examples. The present invention can be used for any purpose where its properties are useful such as in, but not limited to, foods, paper, plastics, adhesives, or paint. From the above discussion and the following examples, one skilled in the art of plant breeding can ascertain, and without departing from the spirit and scope thereof, can make various changes and modifications of the invention to adapt it to various usages and conditions. All such modifications are intended to fall within the scope of the intended claims.

EXAMPLE 1

BREEDING METHODOLOGY FOR PRODUCTION OF GRAIN HETEROZYGOUS FOR THE DULL GENE AND HOMOZYGOUS RECESSIVE FOR THE AMYLOSE EXTENDER AND WAXY GENES

This example illustrates the production of maize grain possessing starch of the present invention. Maize plants of the background LH82 (a product of the Holden's Foundation Seed Co., Williamsburg, Iowa) homozygous recessive for the waxy gene were pollinated by plants of the background OH43 homozygous recessive for the ae gene. Any maize line with good agronomics and high grain yield which is also homozygous recessive for the waxy gene could be utilized in place of Holden's LH82. Other suitable lines, for example, are B37 waxy and OH43 waxy, which are available from Purdue University, West Lafayette, IN. Progeny of this cross pollination were grown and self pollinated to produce F2 generation seed. Single F2 kernels carrying both the ae and wx genes were selected visually. Kernels carrying both mutant genes are more shrivelled than kernels carrying only one of the two recessive genes. Double mutant kernels were planted and at anthesis were cross pollinated onto maize plants of the background IA453 known to be homozygous recessive for ae, du, and wx to produce the present invention. Seed of the maize plant IA453 have been deposited in the American Type Culture Collection (ATCC), a Budapest Treaty designated depository, Rockville, Md. 20852-1776 on . . . and bears the ATCC accession number . . . This cross pollination produced grain having one copy of the semidominant Dull allele. The reciprocal cross was also made where the triple mutant ae du wx was cross pollinated onto the double mutant ae wx plants, resulting in grain having two copies of the semidominant Dull allele. Double mutant ae wx plants were also self pollinated and have been found to be true breeding for ae and wx.

Grain that is heterozygous for the dull gene and homozygous recessive for the ae and wx genes is referred to as aDx grain, designating that the cells comprising the grain carry at least one copy of the semidominant Dull allele. Starch extracted from grain heterozygous for the dull gene and homozygous recessive for the ae and wx genes is referred to as aDx starch.

EXAMPLE 2

STARCH EXTRACTION AND RHEOLOGY

Starch was extracted from aDx and aewx kernels that were produced as described in Example 1. For each sample, 15.0 g of undamaged kernels were weighed into a 50 mL Erlenmeyer flask. Forty mL steep solution, prepared by adding 1% lactic acid and 0.3% sodium metabisulfite to water (w/v) and adjusting to pH 3.82 with NaOH, was added. The tightly-stoppered flasks were held at 52° C. for 18–24 hours, then the kernels were drained and rinsed with water. The pericarps and germs were removed from each kernel with a sharpened spatula. A filtration apparatus was prepared by stretching a 72 micron mesh screen over a 15 cm plastic funnel using a rubber band then placing the stem of the funnel into a 1 liter beaker. The degerminated kernels were placed into a 120 mL square glass bottle and about 50 mL of 50 mM NaCl was added. Using a 20 mm Polytron probe (Kinematica GmbH: Kriens-Luzern, Switzerland) the kernels were alternately ground and filtered through the mesh until microscopic examination of the residue on the mesh showed no intact starch-bearing cells. The speed and duration of grinding were increased until this occurred, starting with 30 seconds at half speed and increasing to 90 seconds at full speed. Usually 4–5 grinds were needed, and about 30 g of ice was added for the full-speed grinds to prevent overheating. The combined filtrate in the beaker was brought to 400 mL with 50 mM NaCl and an equal volume of toluene was added. The mixture was stirred with a magnetic stir-bar for 1 hour at sufficient speed to completely emulsify the 2 phases. The beaker was covered with aluminum foil and the phases allowed to separate overnight. The upper toluene layer was aspirated from the beaker. The starch slurry remaining in the bottom of the beaker was resuspended, poured into a 250 mL centrifuge bottle, and centrifuged 15 minutes at 25,000 RCF. After discarding the supernatant, the starch was washed sequentially with water and acetone by shaking and centrifuging as before. The acetone was decanted and the starch allowed to dry overnight in a fume hood at room temperature.

A Rapid Visco Analyzer ("RVA" Newport Scientific: Sydney, Australia) with high sensitivity option and ThermoCline software was used for pasting curve analysis using the following temperature profile: Idle temperature 50° C. hold 0.5 minutes at 50° C. linear heating to 95° C, over 4 minutes, hold at 95° C. for 2.5 minutes, linear cooling to 50° C. over 4 minutes, hold at 50° C. for 4 minutes.

Figure 2:
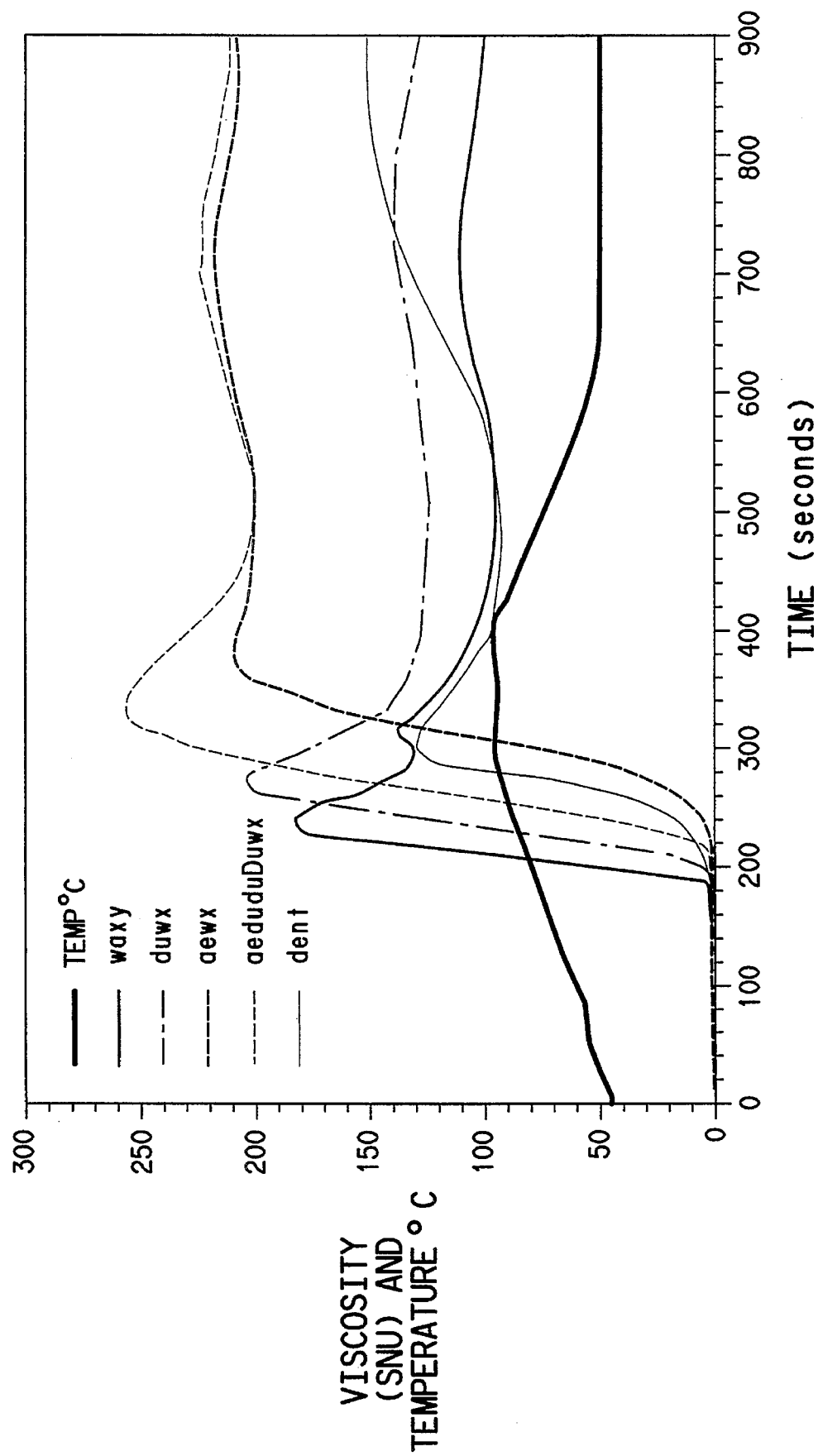
FIG. 2 shows the pasting curves for the starch obtained from normal and mutant maize kernels wherein the viscosity in stirring number units (SNU) and temperature (degrees Celsius) have been measured and plotted as a function of time (in seconds).
Figure 3:
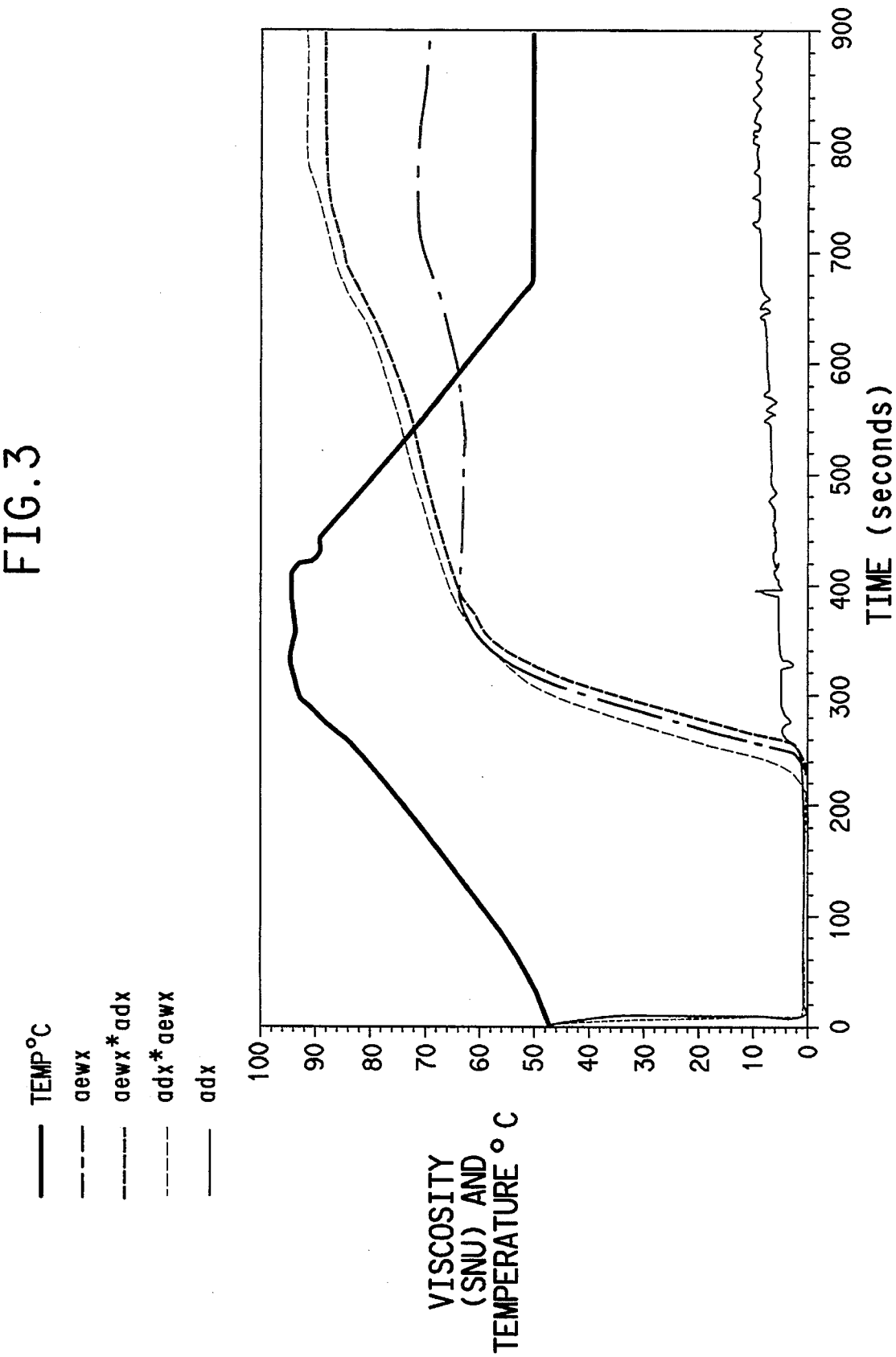
FIG. 3 shows the pasting curves for the starch obtained from mutant maize kernels homozygous recessive for the ae and wx genes, but having varying doses of the dull alleles, wherein the viscosity in stirring number units (SNU) and temperature (degrees Celsius) have been measured and plotted as a function of time (in seconds).
Figure 4:
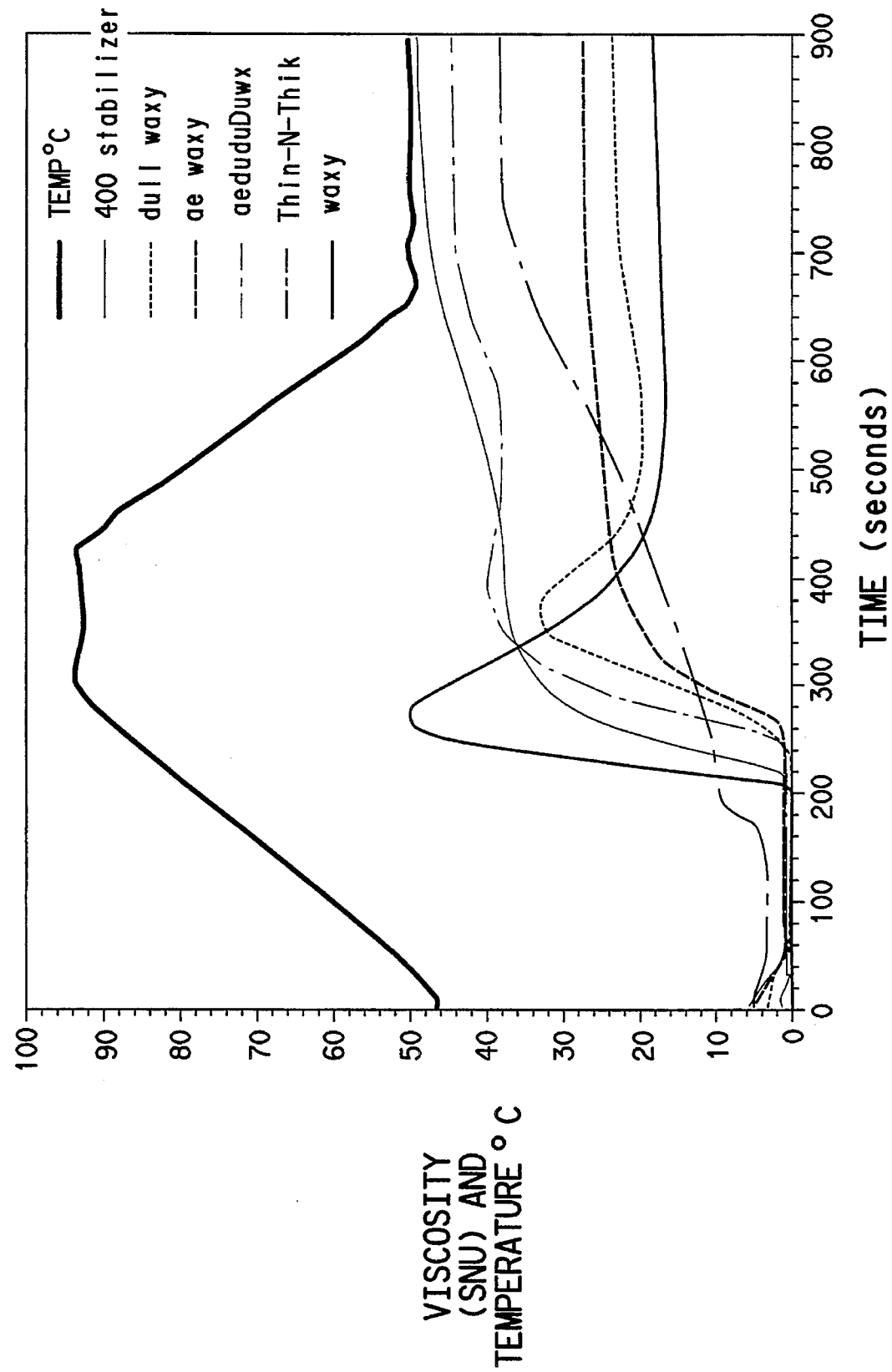
FIG. 4 shows the pasting curves for two chemically modified miaze starches and four starches obtained from maize mutants wherein the viscosity in stirring number units (SNU) and temperature (degrees Celsius) have been measured and plotted as a function of time (in seconds).

The unique properties of the starch of the present invention are shown by the pasting curves (also referred to as RVA profiles) of 2 grams of starch in 20 ml of water (see FIG. 2). FIGS. 2 and 3 show RVA profiles of aDx starch. Also shown in FIG. 2 are RVA profiles for starch extracted from normal dent maize kernels and from kernels homozygous for wx, ae wx, and du wx. Following the initial discovery of the unique properties of aDx starch, RVA analyses shown in FIG. 3 were conducted using 1.5 g starch in 25 ml phosphate-citrate buffer at pH 6.5 to more closely approximate industry standards for starch analysis. FIG. 3 compares RVA profiles of starch of the reciprocal crosses ae du wx X ae wx from grain in which cells of the endosperm contained one copy of the semidominant dull allele, and ae wx X ae du wx from grain in which cells of the endosperm contained two copies of the semidominant dull allele, plus starch from grain homozygous recessive ae du wx. FIG. 4 shows RVA profiles in a simulated acidic food product formulation, using citrate buffer at pH 2.95 with 15% sucrose and 5% starch. The RVA curves show that aDx starch most closely approximates the viscosity and stability of 400 Stabilizer, a chemically cross linked starch. Also, aDx exhibits much higher viscosity than aewx starch and has greater stability than waxy or duwx starch.

Two rheology tests, strain sweep and viscometry, were conducted to further explore the unique properties of aDx starch and compare it with aewx starch. The tests were conducted with starch paste samples (5% dry solids basis) that were cooked in an RVA for 15 minutes at the time-temperature profile described above. After cooking and prior to rheology testing, samples were held for one hour in a 25° C. water bath. Strain sweep and viscometry tests were conducted at 25° C. with a Bohlin VOR rheometer (Bohlin Instruments, Cranbury, N.J.) using a C14 couette geometry. Bohlin software, BRS4.1, was used to collect and manipulate data, and the Jobstream option in the software was used to perform the strain sweep and viscometry tests. The sample was loaded in the C14 cup so that at least 1 mm thick layer stayed above the bob. To prevent moisture loss from the sample, a solvent trap (Bohlin Instruments) was used. To eliminate the effect of loading, the sample was then sheared for 30 seconds at a low shear rate ($18^{s-1}$). Then a programmed delay time (at least 5 minutes) was used to let the sample recover and the strain sweep test was performed. After the strain sweep test, and following another delay time, the viscometry test was performed on the same sample. The same experimental parameters and conditions were used for all samples tested.

The strain sweep test is a dynamic sinusoidal oscillation test that was conducted a 1 Hz frequency applying strain over the range 0.02% to 20%. The output from the test contains elastic and viscous moduli, phase lag, and dynamic viscosity at each of the various strains.

Plasticity, yield strain, gel quality, and gel strength were calculated from the strain sweep data (Table 1). RVA and rheological analyses demonstrate that aDx starch has substantially different rheological properties than aewx starch. The aDx starch pasted at a lower temperature than aewx starch (83° C. compared to 87° C.), and aDx granules swell approximately 50% faster, resulting in higher viscosity at 95° C. On cooling from 95° C. to 50° C., aDx starch has a substantially higher viscosity than aewx starch. The shear thinning and shear stability characteristics were similar for aDx and aewx starch. Both starch types displayed similar gel strength at no strain. However, aewx paste becomes a very weak gel (rigidity decreased by 50% compared to 20% decrease for aDx paste) under a small amount (20%) of strain.

EXAMPLE 3

PRODUCTION OF AN ACIDIC FOOD PRODUCT CONTAINING STARCH OF THE PRESENT INVENTION

This example demonstrates superior food application use of the starch obtained from a plant which is homozygous recessive for the amylose extender and waxy genes and heterozygous for the dull gene (aDx). This starch serves to thicken a cholesterol-free lemon pie filling, affording superior functionality than either a cross-linked waxy starch or a commercially available dull waxy starch.

Fillings for three pies were made, differing only in the starch used. The three starches used were 400 Stabilizer; Amaizo 2522F; and aDx starch. The 400 Stabilizer is a cross-linked waxy maize starch, and Amaizo 2522F is starch from maize ears homozygous recessive for the dull and waxy genes, both are sold by American Maize-Products Company, Hammond, IN. The aDx starch was extracted as in Example 2 from maize ears homozygous recessive for amylose extender and waxy and heterozygous for dull, which were produced by pollinating amylose aeduwx ears with pollen from aewx maize plants.

Pie fillings were made by combining ingredients listed in Table 2 and heating to 88° C. while stirring at 120 RPM. The fillings were held at 88° C. while stirring for 3 minutes, sealed into containers, and cooled to 4° C. After 18 hours, two rheology tests, strain sweep and viscometry, were conducted. The fillings were also poured into pre-baked crusts for visual evaluation.

TABLE 2

Ingredients used to make pie filling of Example 3.

| Ingredient | % | grams |
| --- | --- | --- |
| Water | 60.0 | 300.0 |
| Sugar | 15.0 | 75.0 |
| Lo-Dex 5 (American Maize-Products Co.) | 7.5 | 37.5 |
| Corn syrup, Karo light | 5.0 | 25.0 |
| Starch (see below) | 5.0 | 25.0 |
| Shortening, Crisco (melted) | 4.6 | 23.0 |
| Maltose | 1.75 | 8.75 |
| Lemon extract | 0.70 | 3.50 |
| Citric acid | 0.25 | 1.25 |
| FD&C yellow #5, 4% solution | 0.10 | 0.50 |
| sodium benzoate | 0.10 | 0.50 |

Experimental methods of the strain sweep and viscometry tests are provided in Example 2. To study the shelf stability

TABLE 1

Rheological properties of aDx and aewx starch. Rheological data for aDx starch are an average of three replicates.

| Starch Type | Plasticity (Pa) | Gel Quality (No Strain) | Gel Quality (20% Strain) | Gel Strength (Pa) (No Strain) | Gel Strength (Pa) (20% Strain) | Yield Strain |
| --- | --- | --- | --- | --- | --- | --- |
| aDx | 0.1718 | 0.1723 | 0.2779 | 70.89 | 56.05 | .072 |
| aewx | 1.6172 | 0.0731 | 1.1765 | 51.21 | 26.25 | .099 |

Under no strain, aewx paste displays a somewhat higher solid-like behavior than aDx paste, but exhibits a very high degree of liquid-like behavior under a small strain, whereas aDx paste maintains a solid-like behavior. (See Table 1 plasticity and gel quality values.)

of the pie fillings, samples of each were refrigerated for one week, then rheology tests were conducted at 25° C. Results of the rheological properties of fresh and week-old lemon pie fillings are shown in Table 3. Conclusions that can be drawn from the plasticity, yield strain, gel quality, and gel strength are that aDx starch produces a smoother, more shelf stable lemon pie filling than duwx or 400 Stabilizer starch.

little body, the Amaizo 2522F filling was judged excessively snotty, while the filling made with aDx starch presented a

TABLE 3

Rheological properties of fresh and week old lemon pie fillings using aDx, 400 Stabilizer, and duwx starches.

| Starch Type | Plasticity (Pa) | Gel Quality (No Strain) | Gel Quality (20% Strain) | Gel Strength (Pa) (No Strain) | Gel Strength (Pa) (20% Strain) | Yield Strain |
|---|---|---|---|---|---|---|
| aDx | 0.5741 | 0.1618 | 1.0741 | 100.1 | 39.6 | 0.022 |
| aDx WkOld | 0.7640 | 0.0951 | 1.1852 | 185.8 | 41.9 | 0.022 |
| duwx | 0.1257 | 0.3191 | 0.4118 | 48.5 | 36.8 | 0.050 |
| duwx WkOld | 0.8487 | 0.1734 | 1.0000 | 543.4 | 226.3 | 0.055 |
| 400 | 0.4071 | 0.1905 | 0.3956 | 146.6 | 97.9 | 0.089 |
| 400 WkOld | 0.9064 | 0.1666 | 0.8298 | 177.0 | 61.1 | 0.067 |

All fresh pie fillings had similar gel quality, i.e., solid-like vs. liquid-like, under no strain. At 20% strain, aDx starch displayed a more liquid-like behavior. The week old pie fillings showed considerable changes in their rheological characteristics compared to fresh fillings. Stability is important for commercial applications where a food product remains on a store shelf or in a home refrigerator. The duwx filling showed the greatest plasticity and gel quality change during storage while the aDx filling changed the least. The gel strength of the duwx filling increased dramatically during storage, whereas the aDx and 400 Stabilizer fillings were more stable. The aDx pie filling showed the lowest yield strain of the three, and this value remained stable during the one week refrigeration. Foods displaying low yield strain (such as Crisco) exhibit short texture and creamy mouthfeel.

Texture and visual appearance of the pie filling made with aDx starch was superior to 400 Stabilizer and duwx starch. The 400 Stabilizer presented a runny, thin appearance with full-bodied and lofty pie. These observations reinforce the rheological test results and further demonstrate the novelty and utility of aDx starch.

Details of the preferred embodiments of the present invention have been disclosed for illustration and should not be understood to limit either the spirit of the invention or the scope of the claims. The following claims are intended to cover all modifications of the preferred embodiments of the invention.

What is claimed is:

1. Grain produced by maize in which the genotype of said grain comprises a genome which is homozygous recessive for the waxy gene and the amylose extender gene, and heterozygous for the dull gene.

2. A grain of claim 1 wherein said genome possesses one copy of the semidominant Dull allele.

3. A grain of claim 1 wherein said genome possesses two copies of the semidominant Dull allele.

* * * * *

UNITED STATES PATENT AND TRADEMARK OFFICE
CERTIFICATE OF CORRECTION

PATENT NO. : 5,502,270

DATED : March 26, 1996

INVENTOR(S) : Pearlstein et al.

It is certified that error appears in the above-identified patent and that said Letters Patent is hereby corrected as shown below:

In column 9, line 53 replace "on ... and bears the ATCC accession number ... This cross" with
--on February 23, 1994 and bears the ATCC accession number 75687. This cross--.

Signed and Sealed this

Third Day of June, 1997

BRUCE LEHMAN

Attest:

Attesting Officer

Commissioner of Patents and Trademarks